(12) United States Patent
Chen et al.

(10) Patent No.: US 7,387,765 B2
(45) Date of Patent: Jun. 17, 2008

(54) MICROFLUIDIC CHIP SYSTEM INTEGRATED WITH NANO-ELECTROSPRAY INTERFACE AND METHOD USING THEREOF

(75) Inventors: Shu-Hui Chen, Tainan (TW); Wang-Chou Sung, Kaohsiung (TW); Pao-Chi Liao, Tainan (TW); Gwo-Bin Lee, Tainan (TW)

(73) Assignee: National Cheng Kung University, Tainan (TW)

( * ) Notice: Subject to any disclaimer, the term of this patent is extended or adjusted under 35 U.S.C. 154(b) by 873 days.

(21) Appl. No.: 10/822,650

(22) Filed: Apr. 13, 2004

(65) Prior Publication Data
US 2004/0229377 A1 Nov. 18, 2004

(30) Foreign Application Priority Data
Apr. 14, 2003 (TW) .............................. 92108525 A

(51) Int. Cl.
*B01L 3/02* (2006.01)
*G01N 1/10* (2006.01)

(52) U.S. Cl. ..................... 422/100; 101/68.1; 436/180; 204/604

(58) Field of Classification Search ........ 422/100–101, 422/68.1; 436/180; 204/604
See application file for complete search history.

(56) References Cited

U.S. PATENT DOCUMENTS

| | | | | |
|---|---|---|---|---|
| 6,524,456 B1 * | 2/2003 | Ramsey et al. | ............. | 204/450 |
| 6,642,237 B1 * | 11/2003 | Tata et al. | ............. | 514/252.02 |
| 6,848,462 B2 * | 2/2005 | Covington et al. | ...... | 137/15.01 |
| 7,007,710 B2 * | 3/2006 | Heller et al. | ............. | 137/15.01 |
| 2006/0027744 A1 * | 2/2006 | Stults et al | ................. | 250/288 |
| 2006/0249672 A1 * | 11/2006 | Grimm et al. | .............. | 250/288 |

* cited by examiner

*Primary Examiner*—Brian R. Gordon
(74) *Attorney, Agent, or Firm*—Bacon & Thomas PLLC

(57) ABSTRACT

The present invention provides an integrated microfluidic electrospray chip system and analytical method thereof, characterized in which the proteinase reaction, solid-phase extraction mechanism, electrophoresis and mass spectrometry are integrated into one system. This system allows continuous, fast and on-line detection and identification of a sample, where the sample is firstly hydrolyzed and desalted, and then introduced into the microfluidic electrospray chip to undergo electrophoresis. Finally, the separated sample is introduced into a mass spectrometer by means of electrospray for continuous detection and identification. This system applies mainly in the identification of biochemical substances, such as proteins.

11 Claims, 4 Drawing Sheets

MICROFLUIDIC CHIP SYSTEM INTEGRATED WITH NANO-ELECTROSPRAY INTERFACE AND METHOD USING THEREOF

BACKGROUND OF THE INVENTION

1. Field of the Invention

The present invention relates to an integrated microfluidic electrospray chip system and its analytical method for fast identification of proteins. This system integrates improved protein hydrolysis, solid-phase extraction mechanism, electrophoresis chip and mass spectrometry to provide a continuous protein identification process that produces highly accurate results.

2. Description of Related Art

Capillary electrophoresis (CE) is a kind of widely used analytical technique owing to its advantages of fast separation, minute sample injection volume, high sensitivity and convenient operation [R. Kuhn, S. Hof. Kuhn, Capillary Electrophoresis: Principles and Practice, 1993, Springer-Verlag, Berlin Heidellergg N. Y. (U.S.A.)]. Due to the rapid progression of biotechnology in recent years, analytical techniques developed from capillary electrophoresis have also been widely applied in DNA-based research [Roche, M. E.; Oda, R. P.; Landers, J. P. Biotechnology Progress, 1997, 13, 659-668]. As biochemical technology and semiconductor process technology advanced, Manz applied miniaturized capillary electrophoresis on microchip to undergo sample separation in 1992 [Manz. A.; Harrison, D. J.; Verpoorte, E. M. J.; Fettinger, J. C. I. Paulus, A.; Ludi, H.; Widmer, H. M. J. Chromatogr. 1992, 593, 253-258], and since then, pushed the electrophoretic separation technique to a field of higher technology—chip-based electrophoresis.

Chip-based electrophoresis is a highly efficient assay technique for trace amounts of species [K. Seiler, D. Jed Harrison, A. Manz. Analytical Chemistry 65 (1993), 1481]. There are, for example, reports about depositing purified samples (e.g. PCR (polymerase chain reaction) amplified DNA sequence, enzyme and substrate, antibody and antigen) on the sample channels of biochips for assay [N.-H. Chiem, D. J. Harrison, Electrophoresis (1998), 3040]; [N.-H. Chiem, D. J. Harrison, Clinical Chemistry 44 (3) 591].

Protein identification process is widely applied in drug development and analysis as well as screening of patient specimens. Its primary purpose is to identify unknown protein molecules. For example, flatbed electrophoresis can separate thousands of protein molecules, but cannot identify the proteins from the separated signals. The protein identification process involves the use of proteinase to hydrolyze the protein in the gel into many peptide molecules, which are subject to mass spectrometry to detect the type and sequence of amino acids in the peptide, and then matched against the protein sequence database to decipher the type and source of the protein.

In protein identification process, the first step is to undergo protein hydrolysis. Conventionally it is done by adding proteinase (trypsin) to the protein solution to obtain products of protein digestion after 8-24 hours under 37° C. But for protein reacts with the immobilized proteinase, the protein digested fragments (peptides) and proteinase could be well separated by washing so that the hydrolysis product is free of trypsin to increase the accuracy of a subsequent identification step.

After hydrolysis, the solution contained protein digested fragments must be desalted to have the salt in the buffer removed before being fed to the mass spectrometer for analysis. Usually peptide separation may be achieved by high performance liquid chromatography (HPLC) before detection by mass spectrometry. But the whole process is time consuming and does not allow multianalysis of sample after one injection, which increases the sample consumption and reduces the analysis accuracy.

SUMMARY OF THE INVENTION

To address the drawbacks of prior arts for protein analysis, the present invention provides an integrated microfluidic electrospray chip system, which integrates proteinase reaction, solid-phase extraction mechanism, electrophoresis, and mass spectrometry into the system for protein identification.

The integrated microfluidic electrospray chip system according to the present invention comprises at least: a microfluidic chip having a plurality of microchannels provided thereon for separation of samples; an electrospray nozzle connected to said microfluidic chip for ionization of samples; a hydrolysis unit for the hydrolysis of samples; a solid-phase extraction unit for concentration and purification of samples; a mass spectrometer for analysis and/or identification of samples; and a power supply to supply voltage for use in electrophoresis and electrospray ionization processes.

The microfluidic chip has a plurality of microchannels and fluid reservoirs for feeding and separation of samples; said chip may be made of quartz, glass, silicon chip, polymer or other material having identical effects.

The electrospray nozzle is connected to the end of the fluid reservoir used for storing the separated sample in microfluidic chip, through which the separated sample is ionized and fed into the mass spectrometer.

The hydrolysis unit consists of cartridge-filled proteinase for the hydrolysis of protein samples.

The solid-phase extraction unit is packed with a proper solid phase based on the sample characteristics. For example, a sample is extracted by the stationary phases in the liquid chromatography column and then eluted to the chip for separation before entering mass spectrometer for detection. The solid-phase extraction unit may be connected to the injector or disposed upstream of injector.

Another object of the present invention is to provide a method for rapid protein identification using a microfluidic electrospray chip system, comprising at least the steps of: feeding a sample to a hydrolysis unit to undergo hydrolysis reaction; feeding the hydrolyzed sample into the solid-phase extraction unit to undergo solid-phase extraction; feeding the hydrolyzed and solid-phase extracted sample into the microfluidic chip to undergo electrophoretic separation; feeding the separated sample into the electrospray nozzle to ionize the sample; and feeding the ionized sample into mass spectrometer for instant analysis and identification.

The integrated system according to the present invention has several advantages over conventional protein identification processes: 1. Protein hydrolysis by conventional means takes 2-16 hours, while the method of the present invention takes only 10-20 minutes; 2. The sample may be analyzed several times; in conventional process, one injected sample can only have one single analysis, but the injected sample according to the present invention can have multianalysis. For example, each 20 µL of the injected sample may be repeatedly analyzed six times; 3. Conventional identification process uses chromatography for sample separation, which takes on average 20-60 minutes each time, while the method according to the present invention uses electrophoresis for separation, which takes 3 minutes on average each time; 4. The electrospray ionization in convention process is achieved through sheath gas and flow, while the electrospray according to the present invention does not require such outfit and achieves sample ionization through the working of nozzle; 5. Conventional protein identification process takes 4-24 hours, while according to the present invention, the sample, once separated, may be immediately fed into mass spectrometer for on-line instant detection, hence greatly shortening the process time.

DETAILED DESCRIPTION OF THE INVENTION

Figure 1:
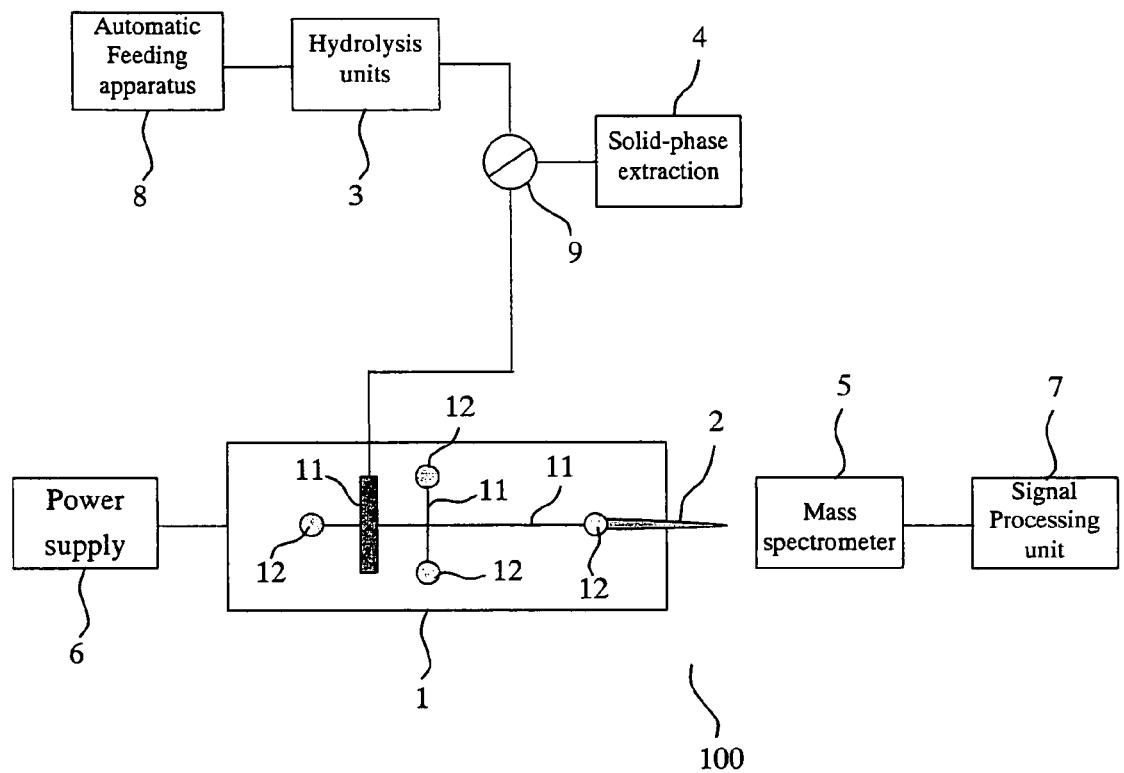
FIG. 1 shows the schematic diagram of an apparatus for the integrated microfluidic electrospray chip system according to the present invention.

As shown in FIG. 1, the integrated microfluidic electrospray chip system 100 according to the present invention comprises at least: a microfluidic chip 1 having a plurality of microchannels 11 provided thereon for separation of samples; an electrospray nozzle 2 connected to said microfluidic chip 1 for ionization of samples; a hydrolysis unit 3 for the hydrolysis of samples; a solid-phase extraction unit 4 for preconcentration and purification of samples; a mass spectrometer 5 for analysis and/or identification of samples; and a power supply 6 to supply the system with voltage for use in electrophoresis and electrospray ionization processes. Signals detected by the mass spectrometer 5 are output through the signal processing unit 7.

The microfluidic chip 1 has a plurality of microchannels 11 and fluid reservoirs 12 for feeding and separation of samples; said chip 1 may be made of quartz, glass, silicon chip, polymer or other material having identical effects.

The electrospray nozzle 2 is connected to the end of one of the fluid reservoirs 12 used for storing the separated sample in microfluidic chip 1 through which the separated sample from the fluid reservoir 12 is ionized and fed into the mass spectrometer 5 for analysis. The electrospray nozzle 2 consists of fused silica capillaries.

The hydrolysis unit 3 consists of cartridge-filled immobilized proteinase, ex. trypsin for the hydrolysis of protein sample. The solid-phase extraction unit 4 is packed with proper solid phase based on the sample characteristics. For example, sample is extracted by the stationary phases in the liquid chromatography column packed with C18 bead or Oligo R3 bead for desalting and then eluted to chip 1 for separation and electrospray ionization before entering mass spectrometer 5 for detection. The solid-phase extraction unit 4 may be connected to the injector 9 which may inject different samples.

Another object of the present invention is to provide a method for rapid protein identification using a microfluidic electrospray chip system. Referring to FIG. 1, the protein sample is introduced into the hydrolysis unit 3 through an automatic feeding apparatus 8 (e.g. pump) to undergo hydrolysis; the hydrolyzed protein is then fed into the solid-phase extraction unit 4 to undergo solid-phase extraction; next, the hydrolyzed and solid-phase extracted protein is fed into the microchannels 11 of microfluidic chip 1 to undergo electrophoretic separation with driving voltage from power supply 6; the separated protein is fed into the electrospray nozzle 2 for ionization; the ionized sample is introduced into the mass spectrometer 5 for instant analysis and identification; and finally the signals obtained from the mass spectrometer 5 are output by the signal processing unit 7.

The integrated microfluidic electrospray chip system and method thereof are further described with the illustration of an example.

EXAMPLE

Experiment Apparatus

Figure 2:
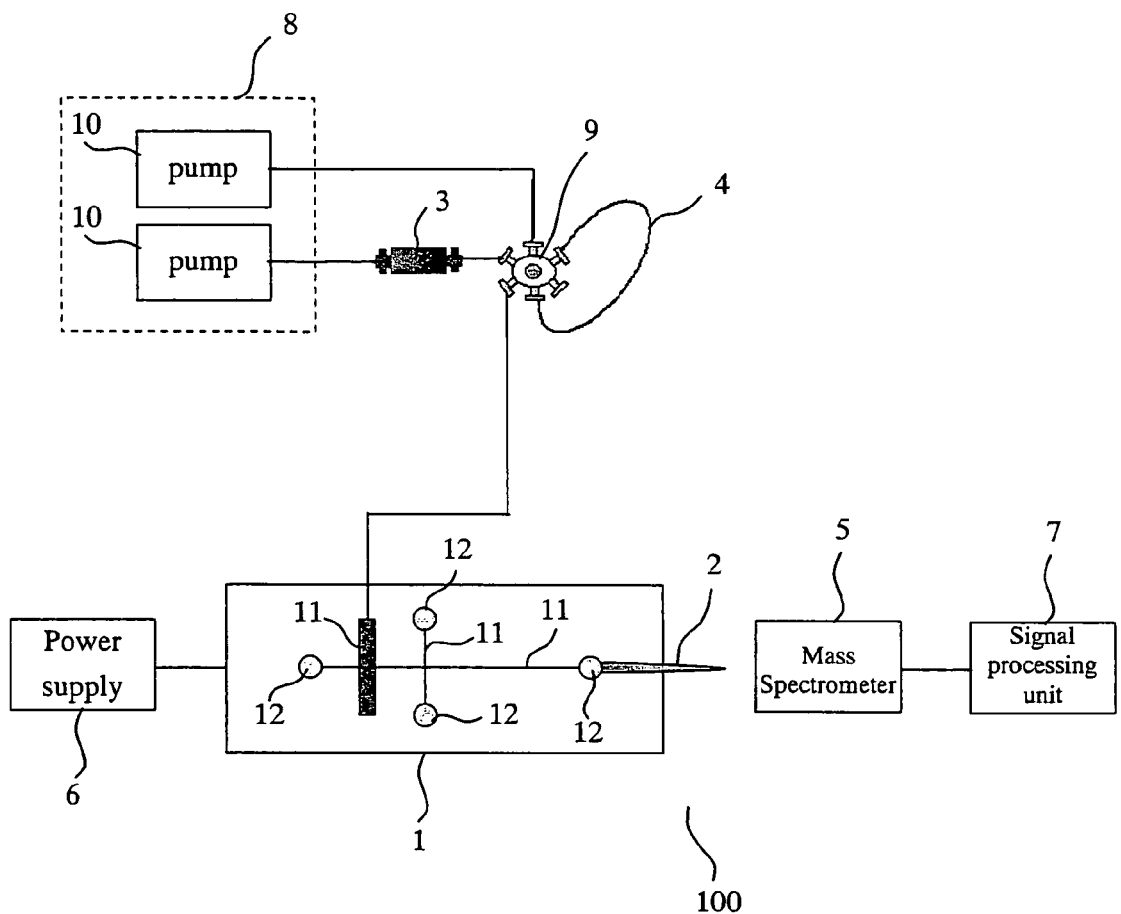
FIG. 2 shows the schematic diagram of an apparatus for the integrated microfluidic electrospray chip system according to an embodiment of the present invention.

In this example, the system as shown in FIG. 2 is used (the equipment arrangement is as shown in FIG. 1). As shown, the automatic feeding apparatus 1 is consisted of two pumps 10; the hydrolysis unit 3 is consisted of a cartridge-filled trypsin as proteinase (trypsin immobilized on porous beads, particle size=40 μm, Pierce 20230); the solid-phase extraction unit 4 was a loop connected to the injector 9 and packed with liquid chromatographic material Oligo R3 beads (Oligo R3 bead, particle size=20 mm, Applied Biosystem 1-1339-03). In this example, two different protein samples (α-lactalbumin and β-casein) are fed into the system for detection.

Procedure

First, two protein samples α-lactalbumin and β-casein are fed separately by the pump 10 into the hydrolysis unit 3. The peptides from the digested proteins are introduced into the solid-phase extraction unit 4 (i.e. the loop) through the injector 9. The hydrophobic region of peptides would react with the hydrophobic groups of Oligo R3 to cause adsorption of peptides to the Oligo R3 bead. Next using low percentage of an organic solvent to wash the bead and desalt, then proceeding with elution by increasing the percentage of the organic solvent to break the peptides from Oligo R3 bead. In the wash and elution procedure, the effect of solid-phase extraction is achieved in the injector loop that results in desalting and purification. Next introducing the sample into the microfluidic electrospray chip 1 for electrophoretic separation. The separated samples enter the electrospray nozzle 2 in sequence for ionization to form positively charged ions. Finally the samples enter the mass spectrometer 5 for detection and analysis.

Results

Figure 3:
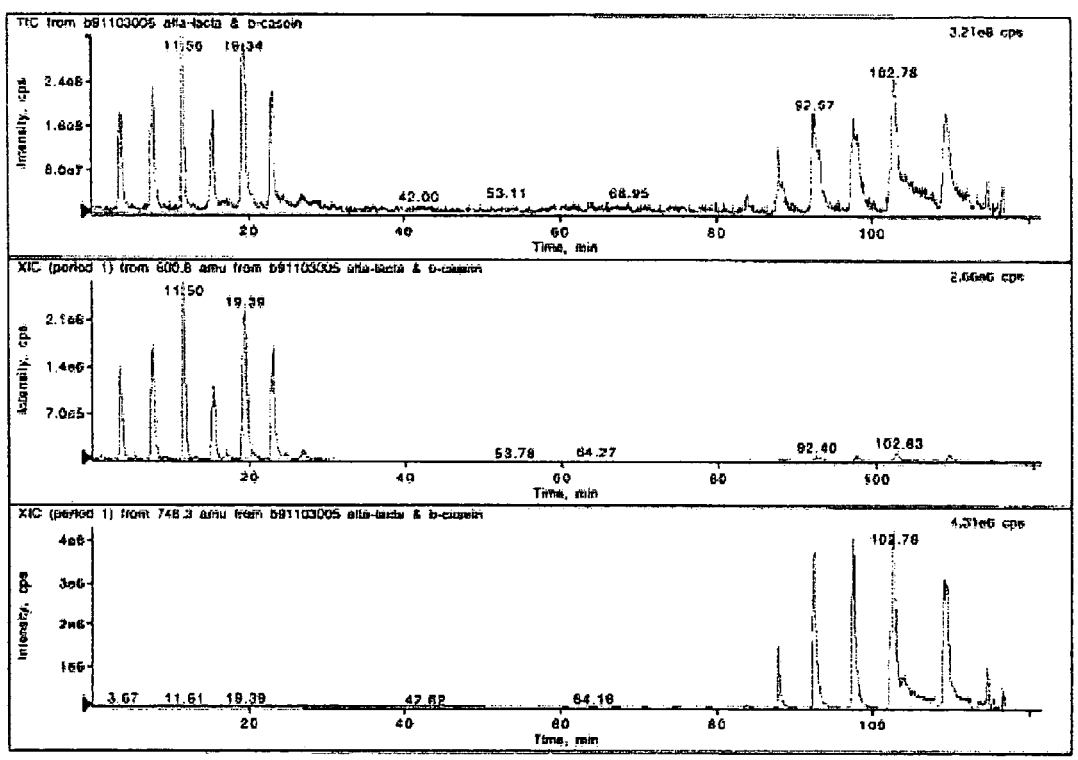
FIG. 3(a) shows the mass spectrum obtained from continuous analysis of α-lactalbumin and β-casein using the system of the present invention.
FIG. 3(b) shows the mass spectrum of α-lactalbumin peptide of specific molecular weight (m/z 600.8).
FIG. 3(c) shows the mass spectrum of β-casein peptide of specific molecular weight (m/z 748.3).
Figure 4:
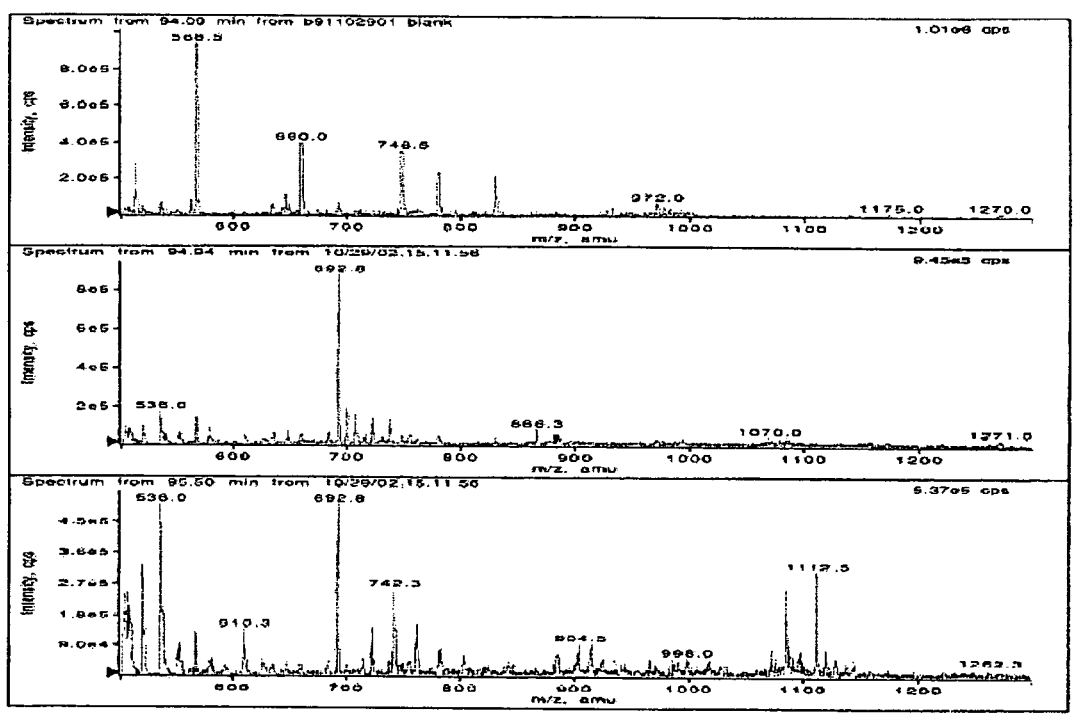
FIG. 4(a) shows the mass spectrum of peptide fragment of β-casein in FIG. 3(a) detected at 94.09 minutes.
FIG. 4(b) shows the mass spectrum of peptide fragment of β-casein in FIG. 3(a) detected at 94.94 minutes.
FIG. 4(c) shows the mass spectrum of peptide fragment of β-casein in FIG. 3(a) detected at 95.50 minutes.

The analysis results are as shown in FIG. 3 and FIG. 4. FIG. 3(a) shows the mass spectrum of two different proteins (α-lactalbumin and β-casein) which are separately and continuously injected into the system. In the example of α-lactalbumin, the amount in one injection may be analyzed continuously six times. Thus this system is suitable for trace amount analysis.

FIG. 3(b) is the mass spectrum of α-lactalbumin peptide of specific molecular weight (m/z 600.8). As shown, when the selected α-lactalbumin peptide of specific molecular weight appeared, the signals of β-casein are not present. Similarly, FIG. 3(c) shows the mass spectrum of β-casein peptide of specific molecular weight (m/z 748.3). When this selected β-casein peptide appears, the signals of α-lactalbumin are not present. Such findings demonstrate that this system can have different samples injected continuously while staying free of signal interference between different samples or the phenomenon of residual signals.

The system according to the present invention can separate sample with electrophoresis. Mass spectrums of samples at different time points of separation can also be obtained. In the case of β-casein, FIG. 4(a) shows the mass spectrum of peptide fragment of β-casein in FIG. 3(a) detected at 94.09 minutes; FIG. 4(b) is the mass spectrum detected at 94.94 minutes; and FIG. 4(c) is the mass spectrum obtained at 95.50 minutes. Based on the results in FIG. 4, it is found that peptides of different molecular weight may be separated by electrophoresis and then detected by the mass spectrometer to add to the accuracy of protein identification.

An embodiment of the present invention has been disclosed in the example. However the example should not be construed as a limitation on the actual applicable scope of the invention, and as such, all modifications and alterations without departing from the spirits of the invention and appended claims shall remain within the protected scope and claims of the invention.

What is claimed is:

1. An integrated microfluidic electrospray chip system, comprising at least:
   a microfluidic chip having a plurality of microchannels provided thereon for separation of samples;
   an electrospray nozzle connected to said microfluidic chip for ionization of samples;
   a hydrolysis unit for the hydrolysis of samples;
   a solid-phase extraction unit for concentration and purification of samples;
   a mass spectrometer for analysis and/or identification of samples; and
   a power supply to supply system voltages for use in electrophoresis and electrospray ionization.

2. The chip system according to claim 1, wherein said microfluidic chip has a plurality of microchannels and fluid reservoirs provided thereon for feeding and separation of samples.

3. The chip system according to claim 1, wherein said microfluidic chip may be made of quartz, glass, silicon chip, polymer or other material having identical effect.

4. The chip system according to claim 2, wherein said electrospray nozzle is connected to the end of one of said fluid reservoirs used for storing the separated sample in said microfluidic chip.

5. The chip system according to claim 1, wherein said hydrolysis unit consists of a cartridge-filled proteinase.

6. The chip system according to claim 5, wherein said proteinase is trypsin.

7. The chip system according to claim 1, wherein said solid-phase extraction unit is packed with Oligo R3 bead or C18 bead or any stationary phase applicable in liquid chromatography.

8. The chip system according to claim 1, wherein said solid-phase extraction unit consists of a loop packed with stationary phases.

9. The chip system according to claim 1, wherein said loop is connected to an injector.

10. The chip system according to claim 1, wherein said electrospray nozzle consists of fused silica capillaries.

11. A chip system according to claim 1, wherein said system integrates proteinase reaction, solid-phase extraction mechanism, electrophoresis and mass spectrometry for protein identification.

* * * * *